United States Patent [19]

Martel et al.

[11] 4,315,943
[45] Feb. 16, 1982

[54] CYCLOPROPYL-CARBOXYLATES USED AS NEMATOCIDES

[75] Inventors: Jacques Martel, Bondy; Jean Tessier, Vincennes, both of France

[73] Assignee: Roussel Uclaf, Paris, France

[21] Appl. No.: 132,836

[22] Filed: Mar. 24, 1980

Related U.S. Application Data

[62] Division of Ser. No. 44,912, Jun. 4, 1979.

[30] Foreign Application Priority Data

Jun. 6, 1978 [FR] France .................................. 78 16858

[51] Int. Cl.³ ............................................. A01N 37/34
[52] U.S. Cl. .................................................... 424/304
[58] Field of Search ......................................... 424/304

[56] References Cited

U.S. PATENT DOCUMENTS 3,835,176  9/1974  Matsuo et al. ...................... 424/306
4,024,163  5/1977  Elliott et al. ...................... 260/347.4
4,100,297  7/1978  Grandadam et al. ............... 424/304

FOREIGN PATENT DOCUMENTS 2384494 11/1978 France .................................. 424/304

*Primary Examiner*—Douglas W. Robinson
*Attorney, Agent, or Firm*—Hammond and Littell, Weissenberger and Muserlian

[57] ABSTRACT

Novel (R,S) and (S)α-cyano-3-phenoxy-benzyl esters of cyclopropane carboxylic acids of the formula

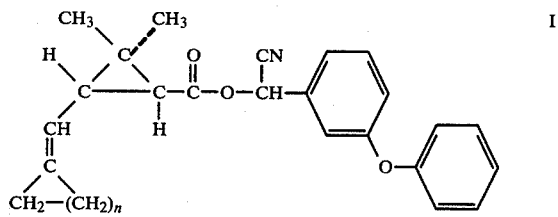

wherein n is an integer from 1,2 or 3 and the acid is (IR, trans) or IR, cis) which have excellent pesticidal activity and their preparation.

2 Claims, No Drawings

CYCLOPROPYL-CARBOXYLATES USED AS NEMATOCIDES

This is a division of Ser. No. 44,912 filed June 4, 1979.

STATE OF THE ART

Related compounds are described in French Pat. Nos. 2,232,273, 2,143,820 and 2,240,914 and in commonly assigned U.S. Pat. No. 4,133,826.

OBJECTS OF THE INVENTION

It is an object of the invention to provide the novel esters of formula I and a novel method for producing the said compounds.

It is another object of the invention to provide novel pesticidal compositions and to provide a novel method of combatting pests.

These and other objects and advantages of the invention will become obvious from the following detailed description.

THE INVENTION

The novel compounds of the invention are (R,S) and (S) α-cyano-3-phenoxy-benzyl esters of cyclopropane carboxylic acids of the formula

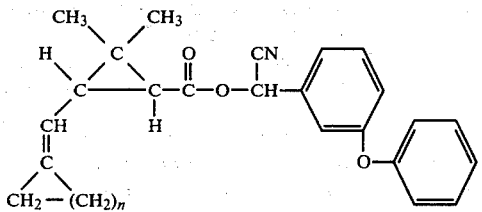

wherein n is an integer from 1,2 or 3 and the acid is (1R, trans) or (1R, cis).

The compounds of formula I contain asymetric carbon atoms in the 1- and 3-positions of the ring and are cis or trans. For convenience reasons, the genus of the structure may be designated in an abbreviated fashion as (1R, cis) or (1R, trans). The alcohol moiety of the compounds of formula I have an asymmetric carbon substituted with the cyano group and this carbon atom has the (R,S) or (S) configuration.

Specific preferred compounds of formula I are (R,S) α-cyano-3-phenoxy-benzyl (1R, trans) 2,2-dimethyl-3-cyclopentylidenemethyl-cyclopropane-1-carboxylate, (S)α-cyano-3-phenoxy-benzyl (1R, trans) 2,2-dimethyl-3-cyclopentylidenemethyl-cyclopropane-1-carboxylate, (R,S)α-cyano-3-phenoxybenzyl (1R, cis) 2,2-dimethyl-3-cyclopentylidenemethylcyclopropane-1-carboxylate, (S)α-cyano-3-phenoxy-benzyl-(1R, cis) 2,2-dimethyl-3-cyclopentylidenemethyl-cyclopropane-1-carboxylate, (R,S)α-cyano-3-phenoxy-benzyl (1R, cis) 2,2-dimethyl-3-cyclobutylidenemethyl-cyclopropane-1-carboxylate, (S)α-cyano-3-phenoxy-benzyl (1R, cis) 2,2-dimethyl-3-cyclobutylidenemethyl-cyclopropane-1-carboxylate, (S)α-cyano-3-phenoxy-benzyl (1R, trans) 2,2-dimethyl-3-cyclobutylidenemethylcyclopropane-1-carboxylate, (R,S)α-cyano-3-phenoxy-benzyl (1R, cis) 2,2-dimethyl-3-cyclopropylidenemethyl-cyclopropane-1-carboxylate, (S)α-cyano-3-phenoxy-benzyl (1R, cis) 2,2-dimethyl-3-cyclopropylidenemethyl-cyclopropane-1-carboxylate, (R,S)α-cyano-3-phenoxy-benzyl (1R, trans) 2,2-dimethyl-3-cyclopropylidenemethyl-cyclopropane-1-carboxylate and (S)α-cyano-3-phenoxy-benzyl (1R, trans) 2,2-dimethyl-3-cyclopropylidenemethyl-cyclopropane-1-carboxylate.

The novel process of the invention for the preparation of the compounds of formula I comprises reacting an acid of (1R, cis) or (1R, trans) structure of the formula

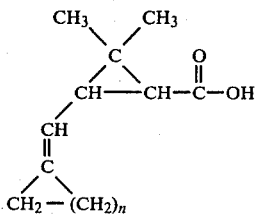

wherein n is 1,2 or 3 or a functional derivative thereof with (R,S) or (S)α-cyano-3-phenoxy-benzyl alcohol to obtain the corresponding ester thereof and in the case of (R,S)α-cyano-3-phenoxy-benzyl alcohol, the ester is reacted with a basic agent in a solvent in which the ester of the (S) alcohol is insoluble and in which the ester of the (R) alcohol is soluble to obtain the ester of (S)α-cyano-3-phenoxy-benzyl alcohol.

In a preferred mode of the process of the invention, the acid halide, especially the chloride, of the acid of formula II is used and the reaction is effected in the presence of a base, preferably a tertiary base such as pyridine or triethylamine in an organic solvent such as benzene.

Another preferred embodiment of the invention comprises reacting the (R,S)α-cyano-3-phenoxy-benzyl ester of formula I with a basic agent in a solvent in which the ester of (S)α-cyano-3-phenoxy-benzyl alcohol is insoluble and in which the (R)α-cyano-3-phenoxy-benzyl ester is soluble to obtain the (S)α-cyano-3-phenoxy-benzyl ester.

The (S)α-cyano-3-phenoxy-benzyl esters may be prepared either by esterification of (S)α-cyano-3-phenoxy-benzyl alcohol with an acid of formula II or a functional derivative thereof or by transformation of (R,S)α-cyano-3-phenoxy-benzyl esters with a basic agent in a solvent in which the ester of the (S) alcohol is insoluble and in which the ester of the (R) alcohol is soluble and recovering by physical means the insoluble ester of the (S) alcohol. The latter transformation is particularly remarkable but it has been generally described in commonly assigned U.S. Pat. No. 4,133,826.

In a preferred mode of the process, the basic agent for the transformation of the (R,S) esters into the ester of the (S) alcohol is selected from the group consisting of ammonium hydroxide, triethylamine, diethylamine, morpholine, pyrrolidine and piperidine as well as catalytic amounts of sodium hydroxide, potassium hydroxide, alkali metal alcoholates, alkali metal amides and alkali metal hydrides and the solvent or mixtures of solvents in which the ester of the (S) alcohol is not soluble is selected from the group consisting of acetonitrile, alkanols, mixtures of alkanols and petroleum ether and especially mixtures of an alkanol and pentane, hexane or heptane. For example, ammonium hydroxide may be used as the base to transform the (R,S) esters into the (S) ester and isopropanol may be the solvent.

The novel pesticidal compositions of the invention are comprised of a pesticidally effective amount of at least one compound of formula I and a carrier. The compositions may contain one or more other pesticide agents and may be in the form of powders, suspensions, emulsions, solutions, aerosol solutions, combustible strips and other preparations classically used for compositions of this type. Especially, preferred are the esters of (S)α-cyano-3-phenoxy-benzyl alcohol.

The compositions may contain a vehicle and/or a non-ionic, surface active agent to ensure a uniform dispersion of the components of the mixture. The vehicle may be a liquid such as water, alcohol, hydrocarbons and other organic solvents, a mineral, animal or vegetable oil or a powder such as talc, clays, silicates, kieselguhr or a combustible solid such as tabu powder (or pyrethrum residue).

The compositions possess interesting insecticidal properties, especially an intense lethal power and are therefore useful against insects in the agricultural field. For example, the compositions are useful against aphis, larvae of lepidopteres and Coleoptera as well as against household insects such as flies and mosquitoes. Tests have shown the compositions to be effective against houseflies, *Spodoptera littoralis*, *Epilachna varivestris*, larvae of *Aedes aegypti*, *Sitophilus granarius* and *Tribolium castaneum*.

The compositions of the invention are also effective nematocides and are useful in the agricultural field for combatting parasitic nematodes in cultivated vegetable fields. Tests have shown the compounds of formula I to be effective against *Ditylenchus myceliophagus*.

The compositions of the invention are also effective acaricides and are useful against parasitic acariens in vegetable fields. Tests have shown the composition to be effective against *Tetranychus urticae*. The compositions are also effective against animal parasitic acariens and are useful against animal parasitic ixodides and sarcoptides, especially against all sorts of mange such as sarcoptic mange, psoroptic mange and chorioptic mange or against all sorts of ticks such as species of Boophilus, Hyalomnia, Amblyoma and Rhipicephalus.

The insecticidal compositions preferably contain classical synergists to increase the activity thereof such as 1-(2,5,8-trioxadodecyl-2-propyl-4,5-methylenedioxy)-benzene or (piperonyl butoxide), N-(2-ethylheptyl)-bicyclo-[2,2,1]-5-heptene-2,3-dicarboximide or piperonyl-bis-2-(2'-n-butoxyethoxy)-ethyl-acetal (tropical). The insecticidal compositions usually contain 0.005 to 10% by weight of the active ingredients.

The nematocidal compositions of the invention containing at least one compound of formula I are in the form of powders, granules, suspensions, solutions or emulsions and may contain other pesticidal agents. For control of nematodes in fields, the compositions are preferably used as liquids for treating soils at a dose of 30 to 500 g/l. The preferred doses for this use is 3 to 300 g of active material per hectare.

The acaricidal compositions of the invention containing at least one compound of formula I may also contain other pesticidal agents as well as a pyrethrinoid synergistic agent and are in the form of powders, granules, suspensions, emulsions, solutions or other usual preparations for this type of composition. The composition may contain a vehicle and/or non-ionic, surface active agent as discussed above.

When used for controlling vegetable parasitic acariens, the compositions are preferably powders or liquids for foliar spraying containing 20 to 80% by weight of active material or powders for foliar dusting containing 1 to 5% by weight of the active material.

The veterinary compositions of the invention for combatting animal parasitic acariens may contain besides the active compounds of formula I pyrethrinoid synergists and may be in the usual veterinary form for external use or digestive or parenteral use.

For topical application, a solution emulsifiable in water which is diluted with water just before use generally contains 1/500 to 1/5 by weight of the active principle and preferably 1/100 to 1/10. The compositions may also contain a large amount of pyrethrinoid synergistic agents as indicated above and may, for example contain 2 to 20 times, preferable 5 to 12 times of piperonyl butoxide than the weight of the active ingredient.

The said solutions generally also contain emulsifiers such as Tween or Span but preferably non-ionic emulsifiers such as Polysorbate 80 or Triton X100 are used. The emulsifying agents play the role of favoring wetting and penetration of the active compounds into the lesions of the skin. Preferably, the amount of emulsifier used is 2 to 20 times, preferably 5 to 10 times, the weight of the active ingredient. The solutions may also contain an antioxidant agent soluble in organic solvents such as Tocopherol acetate. Examples of suitable solvents for the compositions are alcohols such as ethanol, mixtures of ethanol and isopropanol and mixtures of ethanol, isopropanol and ethyl acetate. The usual external dosage varies with the animals treated and the parasites being combatted. A useful dosage for (R,S)α-cyano-3-phenoxybenzyl (1R, trans) 2,2-dimethyl-3-cyclopentylidenemethylcyclopropane-1-carboxylate is 1 part per 1000 parts.

When the compositions are to be administered subcutaneously or intramuscularly, the compositions may be in the form of a solution in normal excipients for that use such as a mixture of benzyl benzoate and arachide oil and injectable solutions may also contain piperonyl butoxide and α-tocopherol acetate. For oral administration, the compositions may be in capsule form or the active compounds may be admixed with the feed for the animals. The animal feed may contain 0.006 to 0.8% by weight of the compounds of formula I and may also contain a synergistic agent.

The novel method of combatting pests comprises contacting the pests or administering to the hostwarm blood animals, a pesticidally effective amount of at least one compound of formula I.

(S)α-cyano-3-phenoxy-benzyl alcohol and its preparation is described in copending, commonly assigned U.S. patent application Ser. No. 973,791 filed Dec. 28, 1978.

In the following examples there are described several preferred embodiments to illustrate the invention. However, it should be understood that the invention is not intended to be limited to the specific embodiments.

EXAMPLE 1

(R,S)α-cyano-3-phenoxy-benzyl (1R, trans) 2,2-dimethyl-3-cyclopentylidenemethyl)-cyclopropane-1-carboxylate 1.5 ml of pyridine were added to a solution of 2.8 g of (R,S)α-cyano-3-phenoxy-benzyl alcohol in 10 ml of anhydrous benzene and a benzene solution of 3.17 g of 1R, trans 2,2-dimethyl-3-(cyclopentylidenemethyl)-cyclopropane-1-carboxylic acid chloride (prepared as in French Pat. No. 1,505,423) was added thereto while keeping the temperature at 20° C. The mixture was stirred for 20 hours and then 20 ml of dilute hydrochloric acid were added thereto. The mixture was extracted with methylene chloride and the organic phase was washed with water, dried and evaporated to dryness. The residue was chromatographed over silica gel and was eluted with a 9-1 cyclohexane-ethyl acetate mixture to obtain 3.5 g of (R,S)α-cyano-3-phenoxy-benzyl (1R, trans) 2,2-dimethyl-3-cyclopentylidenemethyl)-cyclopropane-1-carboxylate with a specific rotation $[\alpha]_D^{20} = -26.5° \pm 2°$ (c=0.7% in benzene).

Analysis: $C_{26}H_{27}NO_3$; molecular weight=401.510: Calculated: %C 77.78; %H 6.78; %N 3.48; Found: %C 77.7; %H 6.9; %N 3.3.

EXAMPLE 2

(S)α-cyano-3-phenoxy-benzyl (1R, trans) 2,2-dimethyl-3-(cyclopentylidenemethyl)-cyclopropane-1-carboxylate 0.2 ml of 22° Baumé ammonium hydroxide solution was added to a mixture of 2 g of the product of Example 1 and 4 ml of isopropanol and the mixture was stirred at 0° C. for 24 hours. Then, 3 ml of petroleum ether (b.p.=60° to 80° C.) were added thereto and the mixture was stirred at −5° C. for 48 hours. The raw mixture was triturated with benzene and the mixture was evaporated to dryness under reduced pressure. The residue was taken up in 4 ml of isopropanol and 0.2 ml of 22° Baumé ammonium hydroxide and the mixture was stirred at −5° C. for 5 days and was then filtered. The crystalline product was rinsed with iced isopropanol and was dissolved in acetone. The solution was evaporated under reduced pressure to dryness to obtain 1.225 g of crystalline (S)α-cyano-3-phenoxy-benzyl (1R, trans) 2,2-dimethyl-3-(cyclopentylidenemethyl)-cyclopropane-1-carboxylate melting at ≃65° C. and having a specific rotation of $[\alpha]_D^{20} = -18° \pm 1°$ (c=1% in benzene). The RMN Spectrum of the crystalline product showed that the product contained about 10% of (R)α-cyano-3-phenoxybenzyl (1R, trans) 2,2-dimethyl-3-(cyclopentylidenemethyl)-cyclopropane-1-carboxylate.

The mother liquors contained unreacted starting material which was determined by its RMN Spectrum and a specific rotation of $[\alpha]_D^{20} = -29°$ (c=1% in benzene).

EXAMPLE 3

(S)α-cyano-3-phenoxy-benzyl (1R, trans) 2,2-dimethyl-3-(cyclopentylidenemethyl)-cyclopropane-1-carboxylate 0.2 ml of triethylamine were added to a mixture of 3.1 g of (R,S)α-cyano-3-phenoxy-benzyl (1R, trans) 2,2-dimethyl-3-(cyclopentylidenemethyl)-cyclopropane-1-carboxylate in 7 ml of isopropanol and the mixture was stirred at 0° C. for 24 hours and at −5° C. for 4 days. The mixture was filtered and the recovered product was rinsed with iced isopropanol and was then dissolved in acetone. The solution was evaporated to dryness under reduced pressure to obtain 1.674 g of (S)α-cyano-3-phenoxy-benzyl (1R, trans) 2,2-dimethyl-3-(cyclopentylidenemethyl)-cyclopropane-1-carboxylate which was identical to the product of Example 2.

EXAMPLE 4

(S)α-cyano-3-phenoxy-benzyl (1R, trans) 2,2-dimethyl-3-(cyclopentylidenemethyl)-cyclopropane-1-carboxylate STEP A: Mixture of (1R,5S) 6,6-dimethyl-4(R)-[(S)-cyano-(3'-phenoxyphenyl)-methoxy]-3-oxa-bicyclo-(3,1,0)-hexan-2-one and (1R,5S) 6,6-dimethyl-4(R)-[(R)-cyano-(3'-phenoxyphenyl)-methoxy]-3-oxa-bicyclo-(3,1,0)-hexan-2-one A mixture of 22.5 g of (R,S)α-cyano-3-phenoxy-benzyl alcohol, 9.46 g of the lactone of cis 2,2-dimethyl-3-(dihydromethyl)-cyclopropane-1R-carboxylic acid and 0.150 g of p-toluene sulfonic acid was heated at 80° C. at a pressure of $10^{-2}$ mm Hg for 2 hours while distilling off the water of reaction and the mixture was then cooled to 20° C. to obtain 30.70 g of raw mixture A containing (1R,5S) 6,6-dimethyl-4(R) -[(S)-cyano-(3'-phenoxyphenyl)-methoxy]-3-oxa-bicyclo (3,1,0)-hexan-2-one and (1R,5S) 6,6-dimethyl-4(R)-[(R)-cyano-(3'-phenoxyphenyl)-methoxy]-3-oxa-bicyclo-(3,1,0)-hexan-2-one with unreacted starting materials as the principal impurity.

STEP B: (1R,5S) 6,6-dimethyl-4(R)-[(S)-cyano-(3'-phenoxyphenyl)-methoxy]-3-oxa-bicyclo-(3,1,0)-hexan-2-one Mixture A of Step A was chromatographed over silica gel and elution with a 95-5 benzene-ethyl acetate mixture yielded 10.9 g of (1R,5S) 6,6-dimethyl-4(R)-[(S)-cyano-(3'-phenoxyphenyl)-methoxy]-3-oxa-bicyclo-(3,1,0)-hexan-2-one melting at 126° C. and having a specific rotation of $[\alpha]_D^{20} = -71°$ (c=1% in benzene).

U.V. Spectrum (ethanol)
Inflexion at 226 nm: $E_1^1 = 319$;
Inflexion towards 267 nm: $E_1^1 = 52$;
Inflex. towards 271 nm: $E_1^1 = 56$;
Maximum at 276 nm: $E_1^1 = 60$;
Inflexion towards 280 nm: $E_1^1 = 48$;

Circular Dichroism (dioxane)
$\Delta\epsilon = -4.2$ at 225 nm (max.)
$\Delta\epsilon = +0.39$ at 287 nm (max.)

RMN Spectrum (deuterochloroform)
Peaks at 1.18–1.23 ppm (hydrogens of geminal methyls); at 1.98–2.08 ppm and 2.15–2.25 ppm (hydrogens of cyclopropyl); at 5.53–5.56 ppm (hydrogen on carbon to which —CN is attached and 4-hydrogen); at 6.91–7.25 ppm (hydrogens of aromatic ring).

STEP C: (S)α-cyano-3-phenoxy-benzyl alcohol 1 g of p-toluene sulfonic acid monohydrate was added to a mixture of 10 g of the product of Step B, 50 ml of water and 100 ml of dioxane and the mixture was refluxed for 23 hours and was then evaporated under reduced pressure to half its original volume. Ether was added to the mixture with stirring and the decanted organic phase was washed with water, dried and evaporated to dryness under reduced pressure. The 9.5 g of residue was chromatographed over silica gel and was eluted with a 9-1 benzene ethyl acetate mixture to obtain 6.1 g of (S)α-cyano-3-phenoxy-benzyl alcohol with a specific rotation of $[\alpha]_D^{20} = -16.5° \pm 1.5°$ (c=0.8% in benzene).

RMN Spectrum (deuterochloroform)
Peaks at 3.25 ppm (hydrogen of alcohol group); at 5.42 ppm (hydrogen of carbon attached to —CN).

STEP D: (S)α-cyano-3-phenoxy-benzyl (1R, trans) 2,2-dimethyl-3-(cyclopentylidenemethyl)-cyclopropane-1-carboxylate 5 ml of pyridine were slowly added at 5° C. to a mixture of 4.38 g of (1R, trans) 2,2-dimethyl-3-(cyclopentylidenemethyl)-cyclopropane-1-carboxylic acid chloride, 4.8 g of the product of Step C and 50 ml of benzene and the mixture was stirred at 20° C. for 20 hours and was then poured into an aqueous hydrochloric acid solution cooled to 5° C. The mixture was extracted with benzene and the organic phase was washed with aqueous sodium bicarbonate solution, with water, dried and evaporated to dryness under reduced pressure. The residue was chromatographed over silica gel and was eluted with a 9-1 petroleum ether (b.p. = 35-70° C.)-ether mixture to obtain 5.08 g of raw product melting at 70° C. The product was crystallized from 6 volumes of isopropanol to obtain 4.2 g of (S)-α-cyano-3-phenoxy-benzyl (1R, trans) 2,2-dimethyl-3-(cyclopentylidenemethyl)-cyclopropane-1-carboxylate melting at 75° C. and having a specific rotation of $[\alpha]_D^{20} = -11° \pm 2°$ (c=0.6% in benzene).

Analysis: $C_{26}H_{27}NO_3$; molecular weight=401.51: Calculated: %C 77.77; %H 6.78; %N 3.49; Found: %C 77.8; %H 6.8; %N 3.3.

RMN Spectrum (deuterochloroform)

Peaks at 1.13–1.20 ppm (hydrogens of geminal methyls); at 1.42 to 1.51 ppm (1- and 3-hydrogens of cyclopropyl); at 1.50 to 1.83 ppm (3'- and 4'-hydrogens of cyclopentyl); at 2.00 to 2.50 ppm (2'- and 5'-hydrogens of cyclopentyl); at 4.95–5.08 ppm (ethylenic hydrogen); at 6.90 to 7.5 ppm (aromatic hydrogens).

Circular dichroism (dioxane)

Δε = −8 at 224 nm (max.); Δε = +0.28 at 283 nm (max.);

Δε = +0.3 at 287 nm (max.).

EXAMPLE 5

(R,S)α-cyano-3-phenoxy-benzyl (1R, cis) 2,2-dimethyl-3-(cyclopentylidenemethyl)-cyclopropane-1-carboxylate Using the procedure of Example 1, 11 g of (R,S)α-cyano-3-phenoxy-benzyl alcohol and 15.3 g of (1R, cis) 2,2-dimethyl-3-(cyclopentylidenemethyl)-cyclopropane-1-carboxylic acid chloride (produced as in French Pat. No. 2,076,204) to obtain after purification by chromatography over silica gel and elution with a 9-1 cyclohexane-ethyl acetate mixture and then with benzene 7.5 g of (R,S)α-cyano-3-phenoxy-benzyl (1R, cis) 2,2-dimethyl-3-(cyclopentylidenemethyl)-cyclopropane-1-carboxylate with a specific rotation of $[\alpha]_D^{20} = +32° \pm 2°$ (c=0.5% in benzene).

Analysis: $C_{24}H_{27}NO_3$; molecular weight=401.507: Calculated: %C 77.78; %H 6.78; %N 3.49; Found: %C 78.1; %H 6.8; %N 3.5.

EXAMPLE 6

(S)α-cyano-3-phenoxy-benzyl (1R, cis) 2,2-dimethyl-B 3-(cyclopentylidenemethyl)-cyclopropane-1-carboxylate Using the procedure of Example 5, 4.4 g of (1R, cis) 2,2-dimethyl-3-(cyclopentylidenemethyl)-cyclopropane-1-carboxylic acid chloride and 4.5 g of (S)α-cyano-3-phenoxy-benzyl alcohol were reacted to obtain after chromatography over silica gel and elution with a 7-3 benzene-cyclohexane mixture 1 g of (S) α-cyano-3-phenoxy-benzyl (1R, cis) 2,2-dimethyl-3-(cyclopentylidenemethyl)-cyclopropane-1-carboxylate with a specific rotation of $[\alpha]_D^{20} = +85.5° \pm 3°$ (c=0.4% in benzene).

Analysis: $C_{26}H_{27}NO_3$; molecular weight=401.507: Calculated: %C 77.78; %H 6.78; %N 3.49; Found: %C 78.0; %H 6.8; %N 3.4.

EXAMPLE 7

(S)α-cyano-3-phenoxy-benzyl (1R, cis) 2,2-dimethyl-3-(cyclobutylidenemethyl)-cyclopropane-1-carboxylate Using the procedure of Example 1, 2.5 g of (1R, cis) 2,2-dimethyl-3-cyclobutylidenemethyl-cyclopropane-1-carboxylic acid chloride (by process of French Pat. No. 1,595,780 by reacting the cis aldehyde with the appropriate phosphorane) and 3 g of (S)α-cyano-3-phenoxy-benzyl alcohol were reacted to obtain after purification by chromatography over silica gel and elution with benzene 1.9 g of (S)α-cyano-3-phenoxy-benzyl (1R, cis) 2,2-dimethyl-3-(cyclobutylidenemethyl)-cyclopropane-1-carboxylate with a specific rotation of $[\alpha]_D^{20} = +95° \pm 3°$ (c=0.54% in benzene) and a melting point of 76° C.

Analysis: $C_{25}H_{25}NO_3$; molecular weight=387.479. Calculated: %C 77.49; %H 6.50; %N 3.61; Found: %C 77.2; %H 6.3; %N 3.5.

EXAMPLE 8

(R,S)α-cyano-3-phenoxy-benzyl (1R, cis) 2,2-dimethyl-3-cyclobutylidenemethyl-cyclopropane-1-carboxylate Using the procedure of Example 1, 2.5 g of (1R, cis) 2,2-dimethyl-3-cyclobutylidenemethyl-cyclopropane-1-carboxylic acid chloride and 3 g of (R,S)α-cyano-3-phenoxy-benzyl alcohol were reacted to obtain after purification by chromatography over silica gel and elution with benzene 2.5 g of (R,S)α-cyano-3-phenoxy-benzyl (1R, cis) 2,2-dimethyl-3-cyclobutylidenemethyl-cyclopropane-1-carboxylate with a specific rotation of $[\alpha]_D^{20} = +47° \pm 0.5°$ (c=2% in benzene).

Analysis: $C_{25}H_{25}NO_3$; molecular weight=387.479: Calculated: %C 77.49; %H 6.50; %N 3.61; Found: %C 77.3; %H 6.3; %N 3.6.

EXAMPLE 9

(S)α-cyano-3-phenoxy-benzyl (1R, cis) 2,2-dimethyl-3-cyclobutylidenemethyl-cyclopropane-1-carboxylate 0.08 ml of triethylamine were added to a mixture of 2 g of (R,S)α-cyano-3-phenoxy-benzyl (1R, cis) 2,2-dimethyl-3-cyclobutylidenemethyl)-cyclopropane-1-carboxylate in 8 ml of isopropanol and crystallization was induced by addition of a few crystals of the desired product. The mixture was stirred for 16 hours at 20° C. and was filtered to obtain 1 g of (S)α-cyano-3-phenoxy-benzyl (1R, cis) 2,2-dimethyl-3-cyclobutylidenemethyl-cyclopropane-1-carboxylate melting at 76° C. and having a specific rotation of $[\alpha]_D^{20} = +99.5°$ (c=0.9% in benzene).

Analysis: $C_{25}H_{25}NO_3$; molecular weight=387.479: Calculated: %C 77.49; %H 6.50; %N 3.61; Found: %C 77.3; %H 6.5; %N 3.7.

The RMN Spectrum in deuterochloroform showed the absence of the ester of (R)α-cyano-3-phenoxy-benzyl alcohol.

EXAMPLE 10

(S)α-cyano-3-phenoxy-benzyl (1R, trans) 2,2-dimethyl-3-cyclobutylidene-cyclopropane-1-carboxylate Using the procedure of Example 1, 2.5 g of (1R, trans) 2,2-dimethyl-3-cyclobutylidene-cyclopropane-1-carboxylic acid chloride (described in French certificate of addition No. 93,112) and 2.2 g of (S)α-cyano-3-phenoxy-benzyl alcohol were reacted to obtain after purification by chromatography over silica gel and elution with a 9-1 petroleum ether-ether mixture 1.2 g of (S)α-cyano-3-phenoxy-benzyl (1R, trans) 2,2-dimethyl-3-cyclobutylidene-cyclopropane-1-carboxylate with a specific rotation of $[\alpha]_D^{20} = -12° \pm 1°$ (c=1% in benzene).

Analysis: $C_{25}H_{25}NO_3$; molecular weight=387.479: Calculated: %C 77.49; %H 6.50; %N 3.61; Found: %C 77.3; %H 6.6; %N 3.5.

EXAMPLE 11

(R,S)α-cyano-3-phenoxy-benzyl (1R, trans) 2,2-dimethyl-3-cyclopropylidenemethyl-cyclopropane-1-carboxylate Using the procedure of Example 1, (1R, trans) 2,2-dimethyl-3-cyclopropylidenemethyl-cyclopropane-1-carboxylic acid chloride prepared from 5.5 g of the corresponding acid (prepared as in French certificate of addition No. 93,112) and 7.5 g of (R,S)α-cyano-3-phenoxy-benzyl alcohol were reacted to obtain after purification by chromatography over silica gel and elution with an 8-2 benzene-petroleum ether mixture 4.2 g of (R,S)α-cyano-3-phenoxy-benzyl (1R, trans) 2,2-dimethyl-3-cyclopropylidenemethyl-cyclopropane-1-carboxylate with a specific rotation of $[\alpha]_D^{20} = -40.5°$ (c=0.8% in chloroform).

Analysis: $C_{24}H_{23}NO_3$; molecular weight=373.428: Calculated: %C 77.19; %H 6.21; %N 3.75; Found: %C 77.1; %H 6.2; %N 3.5.

EXAMPLE 12

(S)α-cyano-3-phenoxy-benzyl (1R, trans) 2,2-dimethyl-3-cyclopropylidenemethyl-cyclopropane-1-carboxylate Using the procedure of Example 1, (1R, trans) 2,2-dimethyl-3-cyclopropylidenemethyl-cyclopropane-1-carboxylic acid chloride prepared from 16 g of the corresponding acid and 27 g of (S)α-cyano-3-phenoxy-benzyl alcohol were reacted to obtain after purification by chromatography over silica gel and elution with an 8-2 benzene-petroleum ether mixture 16.7 g of (S)α-cyano-3-phenoxy-benzyl (1R, trans) 2,2-dimethyl-3-cyclopropylidenemethyl-cyclopropane-1-carboxylate with a specific rotation of $[\alpha]_D^{20} = -38.5° \pm 1.5°$ (c=1% in chloroform).

Analysis: $C_{24}H_{23}NO_3$; molecular weight=373.428: Calculated: %C 77.19; %H 6.21; %N 3.75; Found: %C 77.0; %H 6.1; %N 3.5.

EXAMPLE 13

(R,S)α-cyano-3-phenoxy-benzyl (1R, cis) 2,2-dimethyl-3-cyclopropylidenemethyl-cyclopropane-1-carboxylate Using the procedure of Example 1, (1R, cis) 2,2-dimethyl-3-cyclopropylidenemethyl-cyclopropane-1-carboxylic acid chloride prepared from 3.5 g of the corresponding acid (process of French Pat. No. 1,595,780 from the cis aldehyde and the appropriate phosphorane) and 4.8 g of (R,S)α-cyano-3-phenoxy-benzyl alcohol were reacted to obtain after purification by chromatography over silica gel and elution with an 8-2 benzene-petroleum ether mixture 4 g of (R,S)α-cyano-3-phenoxy-benzyl-(1R, cis) 2,2-dimethyl-3-cyclopropylidenemethyl-cyclopropane-1-carboxylate with a specific rotation of $[\alpha]_D^{20} = +48° \pm 1.5°$ (c=1% in chloroform).

Analysis: $C_{24}H_{23}NO_3$; molecular weight=373.428: Calculated: %C 77.19; %H 6.21; %N 3.75; Found: %C 76.7; %H 6.2; %N 3.7.

EXAMPLE 14

(S)α-cyano-3-phenoxy-benzyl (1R, cis) 2,2-dimethyl-3-cyclopropylidenemethyl-cyclopropane-1-carboxylate Using the process of Example 1, (1R, cis) 2,2-dimethyl-3-cyclopropylidenemethyl-cyclopropane-1-carboxylic acid chloride prepared from 9 g of the corresponding acid and 15 g of (S)α-cyano-3-phenoxy-benzyl alcohol were reacted to obtain after purification by chromatography over silica gel and elution with an 8-2 benzene-petroleum ether mixture 8.6 g of (S)α-cyano-3-phenoxy-benzyl (1R, cis) 2,2-dimethyl-3-cyclopropylidenemethyl-cyclopropane-1-carboxylate with a specific rotation of $[\alpha]_D^{20} = +55.5$ (c=1% in chloroform).

Analysis: $C_{24}H_{23}NO_3$; molecular weight=373.428: Calculated: %C 77.19; %H 6.21; %N 3.75; Found: %C 76.7; %H 6.1; %N 3.6.

EXAMPLE 15

An insecticidal composition was prepared comprised of 3 g of (R,S)α-cyano-3-phenoxy-benzyl (1R, trans) 2,2-dimethyl-3-cyclopentylidenemethyl-cyclopropane-1-carboxylate, 24 g of piperonyl butoxide, 3 g of Tween 80 (sorbitol oleate and its anhydrides polymerized with 20 moles of ethylene oxide for each mole of sorbitol or its anhydride), 0.3 g of 2,4-dimethyl-6-tert.-butyl-phenol and 69.7 g of water.

EXAMPLE 16

A nematocidal composition was prepared in the form of an emulsifiable concentrate for soil treatment consisting of 40% by weight of (R,S)α-cyano-3-phenoxy-benzyl (1R, trans) 2,2-dimethyl-3-cyclopentylidenemethyl-cyclopropane-1-carboxylate, 6.4% of Atlox 4851 (oxyethylene triglyceride with a sulfonate—Acid index of 1.5), 3.2% by weight of Atlox 4855 (oxyethylene triglyceride with a sulfonate—acid index of 3) and 49.6% by weight of xylene.

EXAMPLE 17

An acaricidal composition was prepared in the form of an emulsifiable concentrate consisting of 20% by weight of (S)α-cyano-3-phenoxy-benzyl (1R, cis) 2,2-dimethyl-3-cyclopentylidenemethyl-cyclopropane-1-carboxylate, 6.5% of Atlox 4851, 3.3% of Atlox 4855 and 70.2% by weight of xylene.

EXAMPLE 18

A pharmaceutical composition was prepared in the form of a solution consisting of 5 g of (R,S)α-cyano-3-phenoxy-benzyl (1R, trans) 2,2-dimethyl-3-cyclopentylidenemethyl-cyclopropane-1-carboxylate, 25 g of piperonyl butoxide, 10 g of Polysorbate 80, 25 g of Triton X100, 1 g of Tocopherol acetate and sufficient ethanol for a final volume of 100 ml and the solution is diluted with 5 liters of water when it is to be used.

EXAMPLE 19

A feed base containing a minimum of 11% of raw protein material (2.8% of urea), 2.5% of grass material and a maximum of 15% of cellulosic material, 6% of mineral material and 13% of moisture corresponds to 82 forage units per 100 kilos and also contained per 100 kilos: 910,000 I.U. of vitamin A, 91,000 I.U. of vitamin $D_3$, 156 mg of vitamin E and 150 mg of vitamin C. The feed base was prepared from corn, dehydrated alfalfa, wheat stalks, palm oil molasses press cake, urea and mineral vitamin condiment. To form an animal feed, 0.04 kg of (R,S)α-cyano-3-phenoxy-benzyl (1R, trans) 2,2-dimethyl-3-cyclopentylidenemethyl-cyclopropane-1-carboxylate were added to the feed base.

PESTICIDAL TEST DATA

A. Lethal activity against household flies

The test insects were 4 days old female houseflies which received a topical application of 1 μl of an acetone solution of the test compound to the dorsal thorax with the aid of an Arnold micromanipulator. 30 insects were used for each test and the number of dead insects after 24 hours was determined. The test compounds were used with and without 10 parts of piperonyl butoxide synergist per part of test compound. The results were expressed in $LD_{50}$ on the dose in nanograms necessary to kill 50% of the insects and the results are reported in Table I.

TABLE I

| Active Compound | Dose in mg/l | % Mortality after 24 h | $LD_{50}$ in ng/insects |
|---|---|---|---|
| Compound of | 5 | 93.3 | |
| Example 1 plus | 3.75 | 73.3 | 2.47 |
| synergist | 2.50 | 46.7 | |
|  | 1.25 | 10.0 | |
| Compound of | 5 | 90.0 | |
| Example 1 | 3.75 | 53.3 | 2.28 |
| without | 1 | 26.7 | |
| synergist | 0.75 | 10.0 | |

The data of Table I shows that the compound of Example 1 has a strong lethal effect against household flies.

The test of above was repeated with compounds of Examples 2,5,6,7 and 10 without synergist and the test results are reported in Table II.

TABLE II

| Compound of Example | $LD_{50}$ in ng/insects |
|---|---|
| 2 | 1.57 |
| 5 | 2.5 |
| 6 | 1.47 |
| 7 | 1.56 |
| 10 | 2.77 |

The results of Table II show that the tested compounds possess a strong lethal effect against household flies as well.

B. Knock Down Activity against House Flies

Female house flies about 4 days old were directly sprayed in a Kearns and March chamber with a solution of the test compound in a 1-1 acetone-kerosene mixture using 0.2 ml twice, 50 insects were used for each test. The readings were effected each minute for 10 minutes and then at 15 minutes. The $KT_{50}$ was determined by the usual methods and the results are reported in Table III.

TABLE III

| Compound of Example | $KT_{50}$ in min |
|---|---|
| 5 | 8.6 |
| 6 | 5.9 |
| 7 | 4.8 |
| 10 | 4.4 |
| 11 | 5.1 |
| 13 | 4.9 |

C. Insecticidal Activity against *Spodoptera littoralis* Caterpillars

The test was effected by topical application of 1 μl of an acetone solution of the test compound to the dorsal thorax of each caterpillar using 15 individuals of *Spodoptera littoralis* in the 4th larva stage for each dose. After treatment, the individuals were placed in an artificial nutritive (Poitoit medium) and the number of dead were determined 48 hours later to ascertain the $LD_{50}$ dose in ng. The results are reported in Table IV.

TABLE IV

| Compound of Example | $LD_{50}$ in ng/insect |
|---|---|
| 1 | 1.31 |
| 5 | 2.09 |
| 7 | 2.84 |
| 11 | 3.33 |
| 12 | 2.91 |
| 13 | 3.80 |

The results of Table IV show that the tested compounds have a strong insecticidal activity against larvae of *Spodoptera littoralis*

D. Insecticidal Activity against Larvae of *Epilachna varivestris*

The test was effected by topical application of the test compound as in test C above with penultimate larval stage of *Epilachna varivestris* and after treatment, the larvae were fed bean plants. The number of dead was determined 72 hours after treatment and the results are reported in Table V.

TABLE V

| Compound of Example | $LD_{50}$ in ng/insect |
|---|---|
| 1 | 0.48 (calculated graphically) |
| 5 | 2.5 |
| 7 | 0.53 |
| 11 | 1.66 |

The results of Table V show that the tested compounds have a good insecticidal activity against larvae of *Epilachna varivestris*.

E. Insecticidal Activity against *Aedes aegypti* larvae

Wide mouth bottles of 370 ml volume received 200 ml of water and 1 ml of an acetone solution of the compound of Example 1 was added to each. Each bottle was infested with 10 larvae of *Aedes aegypti* (last larva stage) in 49 ml of water. The degree of efficacy was determined 48 hours after the infestation and during the test, the bottles were at 25° C. in an oven. The results are reported in Table VI.

TABLE VI

| % Mortality 48 hours after dose in ppm | | | | | | | | LD$_{50}$ in ppm |
|---|---|---|---|---|---|---|---|---|
| $10^{-2}$ | $5 \times 10^{-3}$ | $10^{-3}$ | $5 \times 10^{-4}$ | $10^{-4}$ | $5 \times 10^{-5}$ | $10^{-5}$ | $5 \times 10^{-3} >$ | $LD_{50} > 10^{-3}$ |
| 86.6% | 53.3% | 12.9% | 0% | — | — | | | |

Table VI shows that the compound of Example 1 has an interesting insecticidal activity against mosquito larvae.

F. Insecticidal Activity against *Sitophilus granarius* and *Tribolium castaneum*

The test was effected by direct spraying of infested wheat with 5 ml of an acetone solution of the compound of Example 1 and 0.1 ml of water per 100 g of wheat contained in a one liter flask in a rotating (movement) evaporator. The wheat was artifically infested with 50 individuals of either *Sitophilus granarius* or *Tribolium castaneum* and the percentage of dead for each odse was determined after 7 days as compared to untreated controls. The average results for 100 insects was used to determine the LC$_{50}$ (lethal concentration) which is reported in Table VII.

TABLE VII

| Dose in ppm | % efficacy in 7 days | | LC$_{50}$ |
|---|---|---|---|
| | Sitophilus | Tribolium | |
| 10 | 100 | 100 | |
| 7.5 | 100 | 100 | |
| 5.0 | 73.8 | 43.4 | Sitophilus - 4.0 |
| 2.5 | 8.4 | 18.9 | Tribolium - 6.0 |
| 2.0 | 7.0 | 5.0 | |
| 1.5 | 6.1 | 5.1 | |
| 1.0 | 6.1 | 0 | |

The results of Table VII show that the compound of Example 1 possesses a good insecticidal activity against both *Sitophilus granarius* and *Tribolium castaneum* which is remarkable as this activity is about equal against both insects while generally pyrethrinoid type insecticides are clearly less active against Tribolium than Sitophilus.

G. Nematocidal Activity against *Ditylenchus myceliophagus*

The test consisted of placing 0.5 ml of water containing about 2000 nematodes into a flask containing 10 ml of an aqueous solution of the compound of Example 1 and the degree of mortality was determined with a binocular microscope 24 hours after treatment. 3 tests were made corresponding each time to a sample of 1 ml of test solution and the results are reported in Table VIII.

TABLE VIII

| Dose in ppm | % Mortality in 24 hrs. |
|---|---|
| 20 | 100 |
| 10 | 100 |
| 5 | 97.4 |
| 1 | 7.4 |

The results of Table VIII show that the compound of Example 1 has a good nematocidal activity against *Ditylenchus myceliophagus*.

H. Acaricidal Activity against *Tetranychus urticae*

The test was effected on bean leaves infested with 10 female *Tetranychus urticae* per leaf coated about its periphery with glue. The females were left for 24 hours and were then removed and the leaves infested with eggs were divided into 2 groups. The first group was treated with the test compound by spraying of each leaf with 0.5 ml of an aqueous solution with a concentration of 50 or 25 g of the test compound per hectare. The second group of leaves were not treated and served as the control. The number of adults living, eggs living, and living larvae was determined 9 days after the start of the treatment to ascertain the percent of mortality of the adults, eggs and larvae with respect to the controls. The results are reported in Table IX.

TABLE IX

| Compound of Example | % Mortality Adults | % Mortality of laid eggs | % mortality of larvae |
|---|---|---|---|
| 6 | 41.4 | 81.3 | — |
| 7 | 46.1 | 100 | 100 |

The results of Table IX show that the tested compounds have an interesting acaricidal activity against *Tetranychus urticae*.

(a) Activity against acarien parasites of animals

The compounds of Examples 1 and 5 were studied for their activity against *Boophilus microplus* larvae by forming a 10% emulsifiable concentrate in a mixture of dimethylformamide, emulsifiers and Arcopal. The concentrate was diluted with water to concentrations of 1000, 100 and 10 ppm of active compound and the different solutions were used to spray larvae of ticks of tropical cattle of the *Boophilus microplus* type on a spray table. After 24 hours, the number of living and dead larvae was determined to calculate the percent mortality. The results are reported in Table X.

TABLE X

| Dose in ppm | Compound of Example | |
|---|---|---|
| | 1 | 5 |
| 1000 | 100 | 100 |
| 100 | 100 | 100 |
| 10 | 75 | 100 |

(b) Inhibition of Reproduction

The compounds of Examples 1 and 5 were dissolved as in point (a) in the dilutions indicated in Table X and female adult *Boophilus microplus* were dipped for 5 minutes into one of the said dilutions. They were then introduced into a heated chamber for laying eggs. The percentage of ticks which did not lay eggs, the quantity of eggs laid as compared to controls and the percentage of larvae hatching were determined and the percentage of inhibition of reproduction was determined therefrom. 100% indicates total inhibition and 0% indicates the reproduction is the same as the controls. The results are reported in Table XI.

TABLE XI

| Dose in ppm | Compound of Example | |
|---|---|---|
| | 1 | 5 |
| 100 | 92 | 100 |
| 50 | 89 | 100 |
| 25 | 83 | 78 |
| 12.5 | 75 | 65 |
| 6.2 | 82 | 82 |

TABLE XI-continued

| | Compound of Example | |
|---|---|---|
| Dose in ppm | 1 | 5 |
| 3.1 | 50 | 57 |
| 1.5 | 65 | 35 |
| 0.75 | 28 | 43 |
| 0.38 | 21 | 37 |

(c) Systemic activity

The compounds of Examples 1 and 5 dissolved in olive oil were orally administered to guinea pigs at a dose of 25 mg/kg and 1,3 and 5 hours later, fasting bedbugs (*Cimex lectucarius*) were allowed to suck the animals blood. The results of Table XII show the percentage of mortality after 1,3 and 5 hours respectively.

TABLE XII

| | Compound of Example | |
|---|---|---|
| Time in hours | 1 | 5 |
| 1 | — | 10% |
| 3 | 30% | — |
| 5 | 30% | 20% |

Various modifications of the products and processes of the invention may be made without departing from the spirit or scope thereof and it is to be understood that the invention is to be limited only as defined in the appended claims.

We claim:

1. A method of combatting nematodes comprising contacting namatodes with a nematocidally effective amount of at least one compound selected from the group consisting of (R,S) and (S)α-cyano-3-phenoxy-benzyl ester of the cyclopropane carboxylic acids of the formula

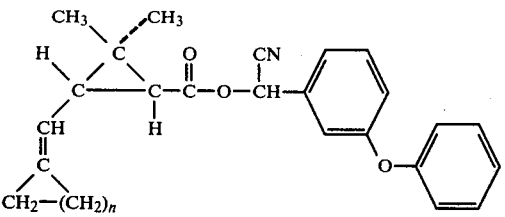

wherein n is an integer from 1,2 or 3 and the acid is (1R, trans) or (1R, cis) by incorporation into soil infested therewith.

2. A method of claim 1 wherein the alcohol portion of the ester is (S)α-cyano-3-phenoxy-benzyl.

* * * * *